US010085954B2

(12) United States Patent
Dansereau et al.

(10) Patent No.: US 10,085,954 B2
(45) Date of Patent: Oct. 2, 2018

(54) QUICK DISSOLVING DIPHENHYDRAMINE ORAL DOSAGE FORM

(71) Applicant: The Procter & Gamble Company, Cincinnati, OH (US)

(72) Inventors: Richard John Dansereau, Cincinnati, OH (US); Brian Laster, Cincinnati, OH (US); Erin Swigart, Morrow, OH (US); Ashraf Traboulsi, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/823,636

(22) Filed: Nov. 28, 2017

(65) Prior Publication Data
US 2018/0078514 A1    Mar. 22, 2018

Related U.S. Application Data

(62) Division of application No. 14/973,759, filed on Dec. 18, 2015, now Pat. No. 9,855,227.

(51) Int. Cl.
| | |
|---|---|
| *A61K 9/00* | (2006.01) |
| *A61K 31/135* | (2006.01) |
| *A61K 9/19* | (2006.01) |
| *A61K 47/12* | (2006.01) |
| *A61K 47/22* | (2006.01) |
| *A61K 31/138* | (2006.01) |
| *A61K 31/4425* | (2006.01) |
| *A61J 1/03* | (2006.01) |

(52) U.S. Cl.
CPC ............ *A61K 31/138* (2013.01); *A61J 1/03* (2013.01); *A61K 9/006* (2013.01); *A61K 9/0053* (2013.01); *A61K 9/0056* (2013.01); *A61K 9/19* (2013.01); *A61K 31/135* (2013.01); *A61K 31/4425* (2013.01); *A61K 47/12* (2013.01); *A61K 47/22* (2013.01)

(58) Field of Classification Search
CPC .................................................. A61K 9/0056
See application file for complete search history.

(56) References Cited

U.S. PATENT DOCUMENTS

| | | | |
|---|---|---|---|
| 4,866,046 | A | 9/1989 | Amer |
| 6,200,604 | B1 | 3/2001 | Pather et al. |
| 7,329,416 | B2 | 2/2008 | Chow et al. |
| 8,097,614 | B2 | 1/2012 | Heit et al. |
| 2006/0073189 | A1 | 4/2006 | Pinney et al. |
| 2006/0141031 | A1 | 6/2006 | Nelson et al. |
| 2009/0155360 | A1* | 6/2009 | Venkatesh ............ A61K 9/0056 424/464 |
| 2009/0263476 | A1 | 10/2009 | Jobdevairakkam et al. |
| 2010/0086495 | A1 | 4/2010 | Rubinstein |
| 2012/0003316 | A1 | 1/2012 | Reddy et al. |
| 2012/0082729 | A1 | 4/2012 | Mezaache et al. |
| 2012/0231092 | A1 | 9/2012 | Oronsky et al. |
| 2013/0095174 | A1 | 4/2013 | Al-Ghananeem |
| 2013/0295175 | A1 | 11/2013 | Chen et al. |
| 2013/0296337 | A1 | 11/2013 | Kothari et al. |
| 2014/0235656 | A1 | 8/2014 | Karavas et al. |

FOREIGN PATENT DOCUMENTS

| | | |
|---|---|---|
| BR | PI0519212 | 1/2009 |
| CN | 102488681 | 3/2013 |
| EP | 1444976 A1 | 8/2004 |
| EP | 2717698 A4 | 1/2015 |
| IN | 2146MUM2010 | 1/2010 |
| RU | 2008127490 A1 | 1/2010 |
| WO | WO2003092591 A2 | 11/2003 |
| WO | WO2009052421 A1 | 4/2009 |
| WO | WO2014196916 A1 | 12/2014 |

OTHER PUBLICATIONS

"Epinephrine (adrenaline) absorption from new-generation, taste-masked sublingual tablets: A preclinical study", J Allergy, Clin. Immunol, Jan. 2013, pp. 236-238.
"Physicochemical properties required for an optimal systemic availability of drugs in relation to the route of administration", Biopharmaceutical aspects of Oral Drug Delivery, Feb. 17, 29164, pp. 19-46.
International Search Report and Written Opinion for PCT/US2016/064367 dated Mar. 23, 2017.
Al-Ghananeem, Abeer M. et al., "Effect of pH on Sublingual Absorption of Oxycodone Hydrochloride", AAPS PharmaSciTech 2006; 7(1) Article 23, pp. E1-E5, Oct. 4, 2005.
Bredenberg, Susanne et al., "In vitro and in vivo evaluation of a new sublingual tablet system for rapid oromucosal absorption using fentanyl citrate as the active substance", European Journal of Pharmaceutical Sciences 20 (2003) pp. 327-334.
Chillas, Stephanie M., "The formulation and evaluation of orally disintegrating tablets: diphenhydramine HCl", The University of Toledo Digital Repository, Theses and Dissertations, 2013 pp. 1-172.
Dali, Manisha M. et al. "A Rabbit Model for Sublingual Drug Delivery: Comparison with Human Pharmacokinetic Studies of Propranolol, Verapamil and Captopril", Journal of Pharmaceutical Sciences, vol. 95, No. 1, Jan. 2006, pp. 37-44.
Dodla, Sumanjali et al., "Buccal Penetration Enhancers—An Overview", Asian Journal of Pharmaceutical and Clinical Research, vol. 6, issue 3, 2013, pp. 39-47.

(Continued)

Primary Examiner — Theodore R. West
(74) Attorney, Agent, or Firm — Amanda Herman

(57) ABSTRACT

An oral dosage form to deliver diphenhydramine through the sublingual or buccal mucosa. The oral dosage form can contain diphenhydramine, or a pharmaceutically acceptable salt thereof, a permeability enhancer, and a buffering agent. The buffering agent can achieve a pH of about 7.0 to about 8.0. The diphenhydramine can completely dissolve within about 2 minutes.

11 Claims, No Drawings

(56) References Cited

OTHER PUBLICATIONS

Gowtham, M. et al., "Formulation and Evaluation of Fast Dissolving Diphenhydramine Hydrochloride Tablets"., International Journal of Drug Formulation and Research, vol. 2, issue 5, Sep.-Oct. 2011, pp. 309-319.

Hirani, Jaysukh et al., "Review Article Orally Disintegrating Tablets: A Review," Tropical Journal of Pharmaceutical Research, Apr. 2009, 8 (2), pp. 161-172.

Narang, Neha et al. "Sublingual Mucosa As a Route for Systemic Drug Delivery", International Journal of Pharmacy and Pharmaceutical Sciences. vol. 3, Suppl 2, 2011, pp. 18-22.

Rachid, Ousama et al., "Rapidly-disintegrating sublingual tablets of epinephrine: Role of non-medicinal ingredients in formulation development", European Journal of Pharmaceutics and Biopharmaceutics, 82 (2012 pp. 598-604.

Sri, K. Vijaya et al., "Diphendramine Hydrochloride Oral Dispersible Tablets: Preparation and Evaluation", Asian J. Pharm. Res. 2014., vol. 4, issue 3, pp. 123-128.

Wang, Yanfeng et al. "HO-1-u-1 model for screening sublingual drug delivery-Influence of pH, osmolarity and permeation enhancer", International Journal of Pharmaceutics 370 (2009) 68-74.

Zhang, Hao et al., "Oral Mucosal Drug Delivery Clinical Pharmacokinetics and Therapeutic Applications", Clin Pharmacokinet 2002; 41 (9), pp. 661-680.

All Office Actions from U.S. Appl. No. 14/973,759, filed Dec. 18, 2015.

\* cited by examiner

QUICK DISSOLVING DIPHENHYDRAMINE ORAL DOSAGE FORM

FIELD OF THE INVENTION

The invention is generally directed to an oral dosage form of diphenhydramine, and more particularly to a quick dissolving form of diphenhydramine that allows for sublingual or buccal delivery of diphenhydramine.

BACKGROUND OF THE INVENTION

Many people experience problems falling asleep and want a medication that provides fast relief. There are many over-the-counter oral sleep aids that are available, however, they do not provide the fast action consumers desire. Standard oral dosage forms of diphenhydramine, a commonly used sleep aid, are swallowed and absorbed through the gastrointestinal (GI) system. Such forms take at least 30 to 45 minutes for the consumer to experience relief. The lag time between drug administration and onset of action can be attributed to dissolution in the GI tract and absorption into systemic circulation. Slow time to symptom relief for conventional oral dosage forms is often unacceptable to consumers.

Quick disintegrating tablets are an appealing alternative dosage form to consumers. Orally disintegrating tablets are formulated to disintegrate and disperse in the oral cavity prior to release of the active ingredient. The active ingredient can then be swallowed and later absorbed through the GI system like traditional oral dosage forms. Alternatively, the active ingredient can dissolve in saliva and be absorbed via the oral mucosa directly into systemic circulation. Such formulations are able to circumvent the first-pass metabolism effect, which increases the bioavailability of active ingredients.

However, current diphenhydramine products, including disintegrating dosage forms, are formulated to prevent dissolution in the oral cavity because it would cause an unpleasant bitter taste and numbing of the oral cavity. In addition, the biopharmaceutical properties of diphenhydramine at the pH conditions found in the oral cavity (pH 6.0 to 7.0) disfavors oral absorption. As a result, diphenhydramine in these products is swallowed and absorbed through the GI system like traditional dosage forms, which leads to a delay in symptom relief.

As such, there remains a need for improved options for fast acting diphenhydramine medications. In particular, there exists a need for a sublingual or buccal diphenhydramine composition that can dissolve quickly in the oral cavity and can be formulated to increase oral absorption.

SUMMARY OF THE INVENTION

An oral dosage form comprising: (a) a therapeutically effective amount of diphenhydramine or a pharmaceutically acceptable salt thereof; (b) a permeability enhancer selected from the group consisting of sodium caprate, cetylpyridinium chloride, and combinations thereof; and (c) a buffering agent sufficient to achieve a pH of about 7.0 to about 8.0 as determined by the pH Test Method.

An oral dosage form comprising: (a) a therapeutically effective amount of diphenhydramine or a pharmaceutically acceptable salt thereof; and (b) a buffering agent sufficient to achieve a pH within the oral cavity of about 7.0 to about 8.0; wherein the diphenhydramine dissolves within about 2 minutes in a subject's oral cavity.

A package for a pharmaceutical composition comprising: (a) a packaging material and an oral dosage form for sublingual delivery of diphenhydramine or a pharmaceutically acceptable salt thereof contained within the packaging material; wherein the packaging material comprises usage indicia which indicate the steps of (i) placing the oral dosage form under a subject's tongue, (ii) holding the oral dosage form under the tongue for less than about 1 minute, and (iii) swallowing the oral dosage form.

DETAILED DESCRIPTION OF THE INVENTION

Quick disintegrating diphenhydramine products are known. However, current disintegrating diphenhydramine products do not sufficiently dissolve in saliva to be absorbed in the oral cavity. Instead, consumers swallow the disintegrated tablet along with saliva and diphenhydramine passes into the GI system, where traditional absorption processes occur. It has been found that diphenhydramine can be readily absorbed across buccal tissue at a narrow pH range. This can allow for the bypass of first-pass metabolism and can result in higher bioavailability of diphenhydramine.

Under the acidic pH conditions in the oral cavity many compounds are ionized and are not efficiently absorbed across the oral mucosa. Diphenhydramine, which has a pKa of about 9, is highly ionized at low pH conditions and is not readily absorbed in the oral cavity. By adjusting the pH to a range of about 7.4 to about 9.0, permeability of diphenhydramine across buccal tissue can be greatly increased. It is believed that an increase in the rate of absorption can result in a faster onset of action and symptom relief.

The present invention further relates to a method for inducing sleep or providing allergy relief in subjects in need thereof. The method can comprise placing an oral dosage form in the oral cavity of a subject, the oral dosage form including diphenhydramine or a pharmaceutically acceptable salt thereof; a permeability enhancer selected from the group consisting of sodium caprate, cetylpyridinium chloride and combinations thereof; and a buffering agent sufficient to achieve a pH within the oral cavity of about 7.0 to about 8.0. In one example, the method includes administering the oral dosage form sublingually.

In one example, the present invention relates to a method for enhancing oral absorption of diphenhydramine. The method can comprise placing an oral dosage form in the oral cavity of a subject in need of such treatment. The oral dosage form can contain a safe and therapeutically effective amount of diphenhydramine or a pharmaceutically acceptable salt thereof in combination with a suitable buffering agent in an amount that provides a pH of about 7.0 to about 8.0 at the oral mucosa. The diphenhydramine can completely dissolve within about 30 seconds.

The present invention further relates to a package for a pharmaceutical composition including a packaging material and an oral dosage form for sublingual delivery of diphenhydramine contained within the packaging material. The oral dosage form can include diphenhydramine or a pharmaceutically acceptable salt thereof; a permeability enhancer selected from the group consisting of sodium caprate, cetylpyridinium chloride, and combinations thereof; and a buffering agent sufficient to achieve a pH of about 7.0 to about 8.0 at the oral mucosa. The packaging material can include usage indicia that indicate the steps of (i) placing the oral dosage form under a subject's tongue, (ii) holding the oral dosage form under the tongue for less than about 1 minute, (iii) optionally avoiding eating, drinking, and/or talking in order to keep the oral dosage form in place, (iv) swallowing the oral dosage form, (v) optionally administering the oral dosage form at night; (vi) optionally administering the oral dosage form in response to an allergic reaction, and/or (vii) optionally taking the oral dosage form every 4 to 6 hours as needed.

As used herein, "absorption" means penetration of the active ingredient through the oral mucosa and into systemic circulation.

As used herein, "bioavailability" refers to a rate and extent to which the active ingredient or therapeutic moiety is absorbed from a drug product and becomes available for therapeutic action. In one example the active ingredient can be diphenhydramine and it can reach the systemic circulation and can be available at its site of action.

As used herein, "disintegrate" or "disintegrating" means the process whereby an oral dosage form falls apart into smaller aggregates or particles.

As used herein, "dissolve" or "dissolving" means the process whereby a solid becomes incorporated into a liquid so as to form a solution.

As used herein, the term "permeability enhancer" is a material capable of decreasing the penetration barrier of the oral mucosa and enhancing permeation of diphenhydramine through the oral mucosa.

As used herein, "subject" means animals or humans.

As used herein, "therapeutically effective amount" of an active ingredient refers to a non-toxic but sufficient amount of the active ingredient to provide the desired sleep effect and/or response to allergic reaction. The amount of active ingredient that is "effective" will vary from subject to subject, depending on the age and general condition of the individual, the particular active agent or agents, and the like.

As used herein, the articles "a" and "an" are understood to mean one or more of the material that is claimed or described, for example, "a permeability enhancer".

All weights, measurements and concentrations herein are measured at 23 degrees Celsius (° C.) and 50% relative humidity, unless otherwise specified.

All percentages, parts and ratios as used herein are by weight of the total oral dosage form, unless otherwise specified. All such weights as they pertain to listed ingredients are based on the active level and, therefore do not include solvents or by-products that may be included in commercially available materials, unless otherwise specified.

The composition and methods of the present invention can comprise, consist of, or consist essentially of, the essential elements and limitations of the invention described herein, as well as any additional or optional ingredients, components, or limitations described herein or otherwise useful in personal health care articles intended for use or consumption by a subject.

Many active ingredients, including diphenhydramine, are sensitive to pH conditions. For active ingredients that are weakly acidic or weakly basic, the pH of the aqueous environment can influence the relative concentrations of the ionized and unionized forms of the drug present in solution. In general, active ingredients in the unionized form are more readily transported across the mucosal membrane. The fraction of unionized active ingredient present in saliva will determine the rate at which the active is absorbed. Under the acidic pH conditions of the oral cavity, diphenhydramine would be highly ionized and would not be efficiently absorbed into the bloodstream through the oral mucosa. In one example, the pH of the saliva may be adjusted by including a buffering agent in the oral dosage form which can permit the relative portions of the ionized and unionized forms of the drug to be controlled.

In one example, the oral dosage form can include a buffering agent for adjusting the pH conditions to optimize the percentage of unionized diphenhydramine available in the oral cavity, and thus, to modulate the rate of mucosal absorption of diphenhydramine. In one example, the buffering agent can achieve a pH of about 6.0 to about 9.0, in another example from about 6.5 to about 8.5, in another example from about 7.0 to about 8.3, and in another example from about 7.4 to about 8.0. In one example, the buffering agent can achieve a pH of greater than about 6.0, and in another example greater than about 7.0. In one example, the buffering agent can be sufficient to achieve a pH of from about 7.0 to about 8.0. In another example, the buffering agent can be sufficient to achieve a pH of about 7.4. In one example, the buffering agent will not achieve a pH of greater than about 8.0. In one example, the solubility of diphenhydramine can decrease at a pH of greater than about 8.0 and can cause diphenhydramine to precipitate out of solution. This can be undesirable because precipitated diphenhydramine will not be absorbed in the oral cavity and must be swallowed. The resulting pH after an oral dosage form disintegrates and is dissolved into solution can be measured using the pH Test Method described hereafter.

In one example, the oral dosage form can include a buffering agent sufficient to achieve a pH within the oral cavity amenable to diphenhydramine absorption through the oral mucosa. In one example, the oral dosage form can achieve a pH within the oral cavity of about 7.0 to about 8.0, in another example about 7.2 to about 7.8, and in another example about 7.4 to about 7.6.

In one example, the buffering agent can be any basic excipient. Non-limiting examples of buffering agents can include meglumine, glycine, sodium carbonate, calcium carbonate, sodium bicarbonate, phosphate buffer, magnesium hydroxide, and combinations thereof. In one example, the buffering agent is meglumine, glycine, and combinations thereof.

In order to increase the passage of diphenhydramine through the oral mucosa, one or more permeability enhancers may be used. Any permeability enhancers effective in increasing oral permeability may be used. Non-limiting examples of permeability enhancers include bile salts, surfactants, synthetic surfactants, cyclodextrins, solvents, and combinations thereof. In one example, the permeability enhancer can be sodium dodecyl sulfate, polyethylene glycol (PEG)-8 stearate (commercially available from Croda, Inc., Edison, N.J., USA), citrate buffer, oleic acid, sodium caprate, cetylpyridinium chloride, menthol, and combinations thereof. In one example, the permeability enhancer can be sodium caprate, cetylpyridinium chloride, and combinations thereof. In one example, the permeability enhancer can be sodium caprate. In one example the permeability enhancer can be cetylpyridinium chloride. In one example, the permeability enhancer cannot be citrate, oleic acid, sodium dodecyl sulfate, or PEG-8 stearate.

In one example the oral dosage form can contain about 0.1% to about 10% permeability enhancer, in another example from about 0.25% to about 8%, in another example from about 0.3% to about 6%, in another example from about 0.5% to about 3%, and in another example from about 0.75% to about 1.5%. In one example, the oral dosage form can contain about 1% permeability enhancer.

In one example, the apparent permeability coefficient of diphenhydramine across buccal tissue can be from about $2.5 \times 10^{-6}$ cm/s to about $40 \times 10^{-6}$ cm/s as determined by the in vitro Permeability Assay, in another example from about $5\times10^{-6}$ cm/s to about $38\times10^{-6}$ cm/s, in another example from about $10\times10^{-6}$ cm/s to about $35\times10^{-6}$ cm/s, in another example from about $20\times10^{-6}$ cm/s to about $32\times10^{-6}$ cm/s, and in another example from about $22\times10^{-6}$ cm/s to about $30\times10^{-6}$ cm/s.

In one example, the apparent permeability coefficient of diphenhydramine across buccal tissue with a permeability enhancer present in the oral dosage form can be from about 1.2-fold to about 3-fold greater than the apparent permeability coefficient of diphenhydramine without a permeability enhancer present in the oral dosage form. In another example, the apparent permeability coefficient of diphenhydramine across buccal tissue with a permeability enhancer present in the oral dosage form can be from about 1.3-fold to about 2.5-fold greater, in another example from about 1.3-fold to about 2-fold greater, and in another example from about 1.3-fold to about 1.8-fold greater. In one example, the apparent permeability coefficient of diphenhydramine across buccal tissue with a permeability enhancer present in the oral dosage form can be more than 1.3-fold greater than the apparent permeability coefficient of diphenhydramine without a permeability enhancer present in the oral dosage form.

In one example, the ratio of diphenhydramine to permeability enhancer can be greater than about 1:1. In one example, the ratio of diphenhydramine to permeability enhancer can be from about 1:5 to about 1:30, in another example from about 1:10 to about 1:25, and in another example from about 1:12.5 to about 1:20. In one example, the ratio of diphenhydramine to permeability enhancer can be about 1:12.5. In another example, the ratio of diphenhydramine to permeability enhancer can be about 1:25.

The oral dosage form can disintegrate quickly and diphenhydramine can be dissolved in saliva before it is swallowed. One advantage to quick disintegrating oral dosage forms is that they can be easy for pediatric and geriatric patients to use and can allow for the quick release of diphenhydramine. One advantage to quick dissolving diphenhydramine is that it can minimize the possibility that a subject will swallow the diphenhydramine before it is absorbed through the oral mucosa. After administration of the oral dosage form, a subject can only hold the oral dosage form in his or her oral cavity for a short period of time because of the involuntary swallowing reflex. If the dissolution of diphenhydramine is too slow, it could result in an insufficient amount of oral absorption into the bloodstream to achieve quick relief of symptoms.

Current oral diphenhydramine products disintegrate, but do not dissolve in the oral cavity. This is because current products are formulated to bind diphenhydramine or are coated with a polymer to prevent oral dissolution to avoid the unpleasant bitter taste and numbing effect of diphenhydramine. In one example, the oral dosage form cannot be coated with a polymer to prevent dissolution in the oral cavity.

In one example, the oral dosage form can disintegrate in about 1 second to about 3 minutes, in another example in about 5 seconds to about 2 minutes, in another example about 10 seconds to about 1 minute, and in another example in about 15 seconds to about 45 seconds. In one example, the oral dosage form can disintegrate in about 1 minute, in another example in about 30 seconds, and in another example in about 10 seconds. In one example, the oral dosage form can disintegrate in less than about 3 minutes, in another example in less than about 2 minutes, in another example in less than about 1 minute, in another example in less than about 30 seconds, and in another example in less than about 15 seconds. Disintegration can be measured according to the Disintegration Method described hereafter.

In one example, the oral dosage form can be formulated to allow the diphenhydramine to quickly dissolve in saliva. In one example, the diphenhydramine in the oral dosage form can dissolve in saliva in about 1 second to about 5 minutes, in another example in about 10 seconds to about 3 minutes, and in another example in about 15 second to about 1 minute. In one example, the diphenhydramine can dissolve in saliva in about 2 minutes or less, in another example in about 1 minute or less, in another example in about 45 seconds or less, in another example in about 30 seconds or less, and in another example in about 15 seconds or less.

In one example, the diphenhydramine in the oral dosage form can be completely dissolved within about 15 seconds, in another example within about 30 seconds, in another example within about 45 seconds, in another example within about 60 seconds, in another example within about 2 minutes, and in another example within about 5 minutes. Dissolution can be considered complete when 80% of diphenhydramine in the dosage form is dissolved. Dissolution can be measured according to the Dissolution Method described hereafter.

An oral dosage form can be in any form capable of allowing diphenhydramine to quickly dissolve in the oral cavity. Non-limiting examples of oral dosage forms can include tablets, pills, capsules, lyophilized tablets, lozenges, candies, powders, granular substances, films, dispersible fluids, sprays, and quick dissolving fibers, such as polyvinylpyrrolidone and poly(vinyl alcohol). In one example, the oral dosage form can be lyophilized. One advantage to a lyophilized form is that it can allow diphenhydramine to dissolve almost instantly upon contact with saliva. In addition, diphenhydramine in a lyophilized form can dissolve faster than in a tablet form.

The oral dosage form can be formulated to allow diphenhydramine to dissolve within the oral cavity or on various oral mucous membranes of a subject to release its diphenhydramine content. In one example, the mucous membranes can be the sublingual mucosa, in another example the buccal mucosa, in another example the gingival mucosa, and in another example the palatal mucosa.

The oral dosage form may be administered by placing the oral dosage form in a subject's oral cavity. In one example, the oral dosage form can be placed on top of the subject's tongue. In another example, the oral dosage form can be placed inside the subject's oral cavity adjacent to the cheek for buccal administration. In another example, the oral dosage form can be placed between the upper lip and gums to allow for gingival administration.

In one example, the oral dosage form may be administered sublingually to a subject by placing the oral dosage form under the subject's tongue. After the oral dosage form is placed under the tongue, the subject should avoid eating, drinking, and talking in order to keep the oral dosage form in place and avoid swallowing since the saliva may contain dissolved diphenhydramine. In one example, the subject can hold the oral dosage form under the tongue for between about 10 seconds to about 2 minutes before swallowing, in another example for between about 15 seconds to about 1 minute, and in another example for between about 30 seconds to about 45 seconds. In one example, the subject can hold the oral dosage form under the tongue for less than about 1 minute. While still in the oral cavity, diphenhydramine can be absorbed through the mucosa, which is highly vascularised and well suited for absorption of unionized compounds.

One advantage of sublingual and buccal absorption is that it can bypass the exposure of active ingredients to digestive enzymes in the GI system and can avoid first-pass metabolism in the liver. Active ingredients that are absorbed through the oral mucosa have direct access to the systemic circulation and can appear in the bloodstream within minutes. As a result, high bioavailability and a faster onset of action can be achieved as compared to conventional oral products that are swallowed. Consumers desire fast relief of symptoms, including onset of sleep and allergy relief. In one example, symptom relief can occur within about 5 minutes to about 45 minutes of administration of the oral dosage form. In another example, relief can occur within about 8 minutes to about 35 minutes of administration of the oral dosage form, and in another example within about 10 minutes to about 25 minutes.

In one example, the maximum serum diphenhydramine concentration ($T_{max}$) can be reached in about 5 minutes to about 2.2 hours after sublingual administration of the oral dosage form to a subject. In another example, $T_{max}$ can be reached in about 10 minutes to about 1.5 hours, in another example in about 15 minutes to about 1 hour, in another example in about 20 minutes to about 45 minutes, in another example in about 30 minutes to about 40 minutes. In one example, $T_{max}$ can be reached in about 1 minute to about 30 minutes. In one example, $T_{max}$ can be reached within about 20 minutes after sublingual administration of the oral dosage form to a subject. In one example, $T_{max}$ can be reached within about 12 minutes after sublingual administration of the oral dosage form to a subject.

The oral dosage form can be of any desired size, shape, weight, consistency or hardness, bearing in mind that it should not be swallowed before it disintegrates and diphenhydramine can be capable of dissolving quickly in the oral cavity to minimize the possibility that the diphenhydramine will be swallowed before, and instead of, being absorbed through the oral mucosa. Non-limiting examples of shapes can include round, oblong, oval, square, rectangular, diamond, triangular, five-sided, six-sided, seven-sided, eight-sided, irregular, and combinations thereof.

In one example, the oral dosage form can be any size that can easily fit inside the oral cavity and can allow diphenhydramine to dissolve quickly. In one example the dosage form has a surface area from about 300 mm$^2$ to about 1300 mm$^2$, in another example from about 400 mm$^2$ to about 1000 mm$^2$, in another example from about 500 mm$^2$ to about 900 mm$^2$, in another example from about 600 mm$^2$ to about 800 mm$^2$, in another example from about 625 mm$^2$ to about 720 mm$^2$, and in another example from about 650 mm$^2$ to about 700 mm$^2$.

In one example, the particles within the oral dosage form can have a diameter of from about 40 μm to about 400 μm, in another example from about 50 μm to about 300 μm, in another example from about 75 μm to about 250 μm, and in another example from about 100 μm to about 200 μm. In one example, particles within the oral dosage form can have a diameter of about 45 μm. In one example, particles within the oral dosage form can have a diameter of from about 45 μm to about 106 μm. In one example, particles within the oral dosage form can have a diameter of from about 212 μm to about 300 μm. In one example, the particles within the oral dosage form can have a diameter of about 300 μm. While not wishing to be bound by theory, it is believed that a particle size of about 45 μm to about 106 μm can help provide quick dissolution of the active ingredient in a compressed tablet.

In one example, the oral dosage form can have a tablet breaking force (i.e. hardness) sufficient to allow for quick dissolution of diphenhydramine. If the oral dosage form is compacted too tightly, and thus has a high breaking force, the diphenhydramine will dissolve slowly. In one example, the oral dosage form can have a breaking force of less than about 3 kiloponds (kp). In another example the oral dosage form can have a breaking force of less than about 2.5 kp, in another example less than about 2 kp, in another example less than about 1.5 kp, and in another example less than about 1 kp. In one example, the oral dosage form can have a breaking force of about 0.5 kp to about 3 kp, in another example about 0.8 kp to about 2.4 kp, in another example about 1 kp to about 2 kp, and in another example about 1.5 kp to about 1.75 kp. The breaking force can be measured using the Tablet Breaking Force Test Method described hereafter.

In one example, the oral dosage form can contain diphenhydramine or a pharmaceutically acceptable salt thereof as an active ingredient. Non-limiting examples of pharmaceutically acceptable salts can include acetic, benzenesulfonic, benzoic, citric, hydroxyethanesulfonic, fumaric, glutaric, hydrobromic, hydroiodic, hydrochloric, perchloric, malonic, maleic, malic, methanesulfonic, nitric, phosphoric, succinic, sulfuric, tartaric, oxalic, salicylic and the like. In one example, the oral dosage form can contain diphenhydramine hydrochloride (HCL) as an active ingredient. In one example, the oral dosage form can contain diphenhydramine citrate as an active ingredient. In another example, the oral dosage form can contain diphenhydramine tannate as an active ingredient.

In one example, the oral dosage form can contain a therapeutically effective amount of diphenhydramine. In one example, a therapeutically effective amount of diphenhydramine to induce sleep in a standard 50 kg adult can be from about 10 mg to about 50 mg, in another example from about 12.5 mg to about 50 mg, and in another example from about 25 mg to about 50 mg. In one example, a therapeutically effective amount of diphenhydramine to induce sleep in a standard child of age 6 to 12 years can be from about 10 mg to about 35 mg and in another example from about 12.5 mg to about 25 mg. In one example, a therapeutically effective amount of diphenhydramine to counteract allergic responses in a standard 50 kg adult can be from about 12.5 mg to about 50 mg and in another example from about 25 mg to about 50 mg. In one example, the therapeutically effective amount of diphenhydramine to counteract allergic responses in a standard child of age 6 to 12 years can be from about 10 mg to about 35 mg and in another example from about 12.5 mg to about 25 mg.

In one example, the oral dosage form can contain between about 5.0 mg to about 50 mg diphenhydramine, in another example between about 10 mg to about 30 mg diphenhydramine, and in another example between about 12.5 mg to about 25 mg diphenhydramine. In one example, the oral dosage form can contain between about 12.5 mg to about 50 mg diphenhydramine. In one example, the oral dosage form can contain less than or equal to about 50 mg/dose diphenhydramine, in another example less than or equal to about 40 mg/dose, in another example less than or equal to about 30 mg/dose, in another example less than or equal to about 25 mg/dose, in another example less than or equal to about 15 mg/dose, and in another example less than or equal to about 10 mg/dose. In one example, the oral dosage form can contain from about 2.5% to about 25% diphenhydramine, in another example from about 5% to about 15% diphenhydramine, and in another example about 6.25% to about 12.5% diphenhydramine. In one example, the oral dosage form can contain about 12.5% diphenhydramine.

In one example, the oral dosage form can provide a sufficiently high peak blood plasma concentration soon after administration to be effective in the treatment of symptoms. In one example, the oral dosage form can allow for effective diphenhydramine blood plasma concentrations to be achieved even when using lower diphenhydramine doses than administered in currently available oral diphenhydramine products. Many consumers are concerned with the amount of active ingredients they consume and desire low-dose dosage forms that still provide the same benefit.

In one example, the oral dosage form can be consumed one time per day or multiple times per day. In one example, the oral dosage form can be consumed on a daily basis or only as needed when symptoms are present. In one example, the oral dosage form can be consumed every 4 to 6 hours as needed. In one example, the oral dosage form can be consumed at bedtime and in another example the oral dosage form can be consumed after bedtime, especially if a user is having difficulty falling asleep.

In one example, a subject can ingest one tablet per dose, in another example two tablets per dose, and in another example three tablets per dose. In one example, a subject can consume at least one dose per day, in another example at least two doses per day, in another example at least three doses per day, and in another example at least four doses per day. In one example, a subject can consume up to six doses per day.

In one example, the oral dosage form can include one or more additional actives including, but not limited to, decongestants, expectorants, antitussives, pain relievers, and combinations thereof. Non-limiting examples of decongestants can include pseudoephedrine, phenylephrine and any acceptable salt thereof. Non-limiting examples of expectorants can include guaifenesin, ambroxol, bromhexine, and combinations thereof. Non-limiting examples of antitussives can include dextromethorphan, menthol, codeine, chlophedianol, levodropropizine, and combinations thereof. Non-limiting examples of pain relievers can include acetaminophen, ibuprofen, ketoprofen, diclofenac, naproxen, aspirin, and combinations thereof.

The oral dosage form may further comprise a diluent, a disintegrant, a lubricant, or other excipients as would be readily understood in the arts for preparation of a final oral dosage form with the desired hardness and friability characteristics, promote rapid disintegration and dissolution, and/or improve organoleptic properties.

The oral dosage form can comprise a diluent. Non-limiting examples of diluents can include microcrystalline cellulose, silicified microcrystalline cellulose, such as ProSolv® SMCC 90 (commercially available from JRS Pharma, Patterson, N.Y., USA), dextrose, mannitol, sorbitol, maltodextrin, maltitol, and combinations thereof. In one example, the oral dosage form can comprise from about 20% to about 90% diluent, in another example about 30% to about 85%, in another example about 40% to about 83%, in another example about 50% to about 80%, in another example about 60% to about 78%. In one example, the oral dosage form can comprise about 78% diluents.

In one example, the oral dosage form can comprise about 39.5% mannitol and about 39% silicified microcrystalline cellulose. In one example, the ratio of mannitol to silicified microcrystalline cellulose can be from about 1:1 to about 4:1, in another example from about 1.5:1 to about 3.5:1, and in another example from about 1.6:1 to about 3.2:1. In one example the ratio of mannitol to silicified microcrystalline cellulose can be about 1:1. In one example, the ratio of mannitol to silicified microcrystalline cellulose can be about 1.7:1. In one example, the ratio of mannitol to silicified microcrystalline cellulose can be about 3.1:1. While not wishing to be bound by theory, it is believed that the ratio of mannitol to silicified microcrystalline cellulose can help provide a compressed tablet that can maintain its shape and form and not break during packaging.

The oral dosage form can comprise a disintegrant. A disintegrant can be included to formulate a rapid disintegration of the oral dosage form following administration. Non-limiting examples of disintegrants can include crospovidone, sodium starch glycolate, crosslinked sodium carboxymethyl cellulose, low substituted hydroxypropylcellulose, guar gum, sodium alginate, and mixtures thereof. In one example, the oral dosage form can comprise from about 1% to about 20% disintegrant, in another example from about 2% to about 15%, in another example about 2.5% to about 10%, in another example from about 3% to about 8%, in another example from about 3.5% to about 6%. In one example, the oral dosage form can comprise about 4% disintegrant.

In one example, the oral dosage form can comprise mannitol and crospovidone to provide quick disintegration and dissolution. One advantage to using a soluble sugar, like mannitol, is that it can pick up water and dissolve quickly. One advantage to using a disintegrant, like crospovidone, is that it can absorb water and swell, thus causing the tablet to break apart. As a tablet breaks apart it is exposed to liquid, such as saliva in the oral cavity, and can dissolve faster. In one example the ratio of mannitol to crospovidone in the oral dosage form can be about 15:1, in another example from about 13:1, in another example from about 10:1. In one example, the ratio of mannitol to crospovidone in the oral dosage form can be about 9.8:1.

The oral dosage form can comprise a lubricant. Non-limiting examples of lubricants can include sodium stearyl fumarate, magnesium stearate, calcium stearate, zinc stearate, stearic acid, glyceryl behenate, hydrogenated vegetable oils, talc, polyethylene glycol, mineral oil, and combinations thereof. In one example, the oral dosage form can comprise magnesium stearate. In one example, the oral dosage form can comprise from about 0.05% to about 5% lubricant, in another example about 0.1% to about 3%, in another example about 0.25% to about 1.5%, in another example about 0.3% to about 1%, in another example about 0.35% to about 0.75%, and in another example about 0.4% to about 0.6%.

The oral dosage forms can comprise additional excipients, including, but not limited to: binders such as lactose, starch, and corn syrup; glidants such as colloidal silicon dioxide and talc; preservatives and stabilizers.

The oral dosage form can also include a flavoring system to mitigate the bitterness and numbing of diphenhydramine. The flavoring system can comprise sweeteners, sensates, flavoring agents, salivating agents and combinations thereof.

Non-limiting examples of sweeteners can include sucrose, lactose, glucose, fructose, xylose, galactose, maltose, xylitol, sodium saccharin, and high fructose corn syrup. In one example, the oral dosage form can comprise from about 0.5% to about 6% sweetener, another example about 1% to about 5%, in another example about 1.5% to about 4.75%, in another example about 2% to about 4.5%, and in another example about 3% to about 4%. In one example, the oral dosage form can comprise about 4% sucrose.

Non-limiting examples of flavoring agents can include natural flavoring agents, artificial flavoring agents, artificial extracts, natural extracts and combination thereof. Non-limiting examples of flavoring agents can include vanilla, honey, lemon, lemon honey, cherry vanilla, peach, honey ginger, chamomile, cherry, cherry cream, mint, vanilla mint, dark berry, black berry, raspberry, peppermint, spearmint, honey peach, acai berry, cranberry, honey cranberry, tropical fruit, dragon fruit, wolf berry, red stem mint, pomegranate, black current, strawberry, lemon, lime, peach ginger, orange, orange cream, cream sickle, apricot, anethole, ginger, jack fruit, star fruit, blueberry, fruit punch, lemon grass, chamomile lemon grass, lavender, banana, strawberry banana, grape, blue raspberry, lemon lime, coffee, espresso, cappuccino, honey, wintergreen mint, bubble gum, tart honey lemon, sour lemon, sour cherry, green apple, boysenberry, rhubarb, strawberry rhubarb, persimmon, green tea, black tea, red tea, white tea, honey lime, cherry lime, apple, tangerine, grapefruit, kiwi, pear, vanillin, ethyl vanillin, maltol, ethyl-maltol, pumpkin, carrot cake, white chocolate raspberry, chocolate, white chocolate, milk chocolate, dark chocolate, chocolate marshmallow, apple pie, cinnamon, hazelnut, almond, cream, crème brûlée, caramel, caramel nut, butter, butter toffee, caramel toffee, aloe vera, whiskey, rum, cocoa, licorice, pineapple, guava, melon, watermelon, elder berry, oral cavity cooler, raspberries and cream, peach mango, tropical, cool berry, lemon ice, nectar, spicy nectar, tropical mango, apple butter, peanut butter, tangerine, tangerine lime, marshmallow, cotton candy, apple cider, orange chocolate, citral, denatonium benzoate, ethyl maltol, menthol, and combinations thereof.

In one example, the dosage form can comprise from about 0.05% to about 10% flavor, in another example from about 0.1% to about 8%, in another example from about 0.2% to about 6%, in another example from about 0.4% to about 3%, in another example about 0.6% to about 1.5%, in another example about 0.7% to about 1%, and in another example about 0.8% to about 0.9%.

The oral dosage form can be packaged in any suitable packaging material. In one example, the packaging material can include a primary package and/or a secondary package. Non-limiting examples of packaging material can include blister packaging, laminated foil, plastic sachet, a bottle, or a box. In one example, the oral dosage forms can be packaged in single doses so they are easily portable and can be carried in a purse, pocket, or brief case. In another example, the packaging can be substantially rigid which can prevent the oral dosage form from being crushed. In one example, the packaging can be child resistant. In one example, the packaging can be clear.

In one example, the packaging material can include usage indicia to provide usage instructions to a potential user or user of the oral dosage form or package. The indicia can be printed on the primary package and/or the secondary package. The usage indicia can comprise many forms and present the information in many ways and in many types of media. Non-limiting examples of types of indicia include alphanumeric indicia, pictures, drawings, illustrations, photographs, computer-produced images, colors, sounds, textures, shapes, symbols, letters, numbers, and combinations thereof. In one example, the usage indicia can indicate the steps of (i) placing the oral dosage form under a subject's tongue, (ii) holding the oral dosage form under the tongue for less than about 1 minute, (iii) optionally avoiding eating, drinking, and/or talking in order to keep the oral dosage form in place, (iv) swallowing the oral dosage form, (v) optionally administering the oral dosage form at night; (vi) optionally administering the oral dosage form in response to an allergic reaction, and/or (vii) optionally taking the oral dosage form every 4 to 6 hours as needed.

Permeability Test

In order to test the effect of donor pH levels on the unidirectional permeability of diphenhydramine across buccal tissue, the Permeability Test was performed. Cell culture experiments were performed using buccal tissue plated on Millipore Millicell® plates. First, a dosing solution containing diphenhydramine and reference compounds was added to the apical surface of the tissue. Then, the transport of diphenhydramine and reference compounds across the tissue was monitored over time by sampling the donor and receiver solutions. The test was performed according to the Permeability Assay as described hereafter.

Table 1 summarizes the results from this test.

TABLE 1

Unidirectional Permeability of Diphenhydramine at varying pH conditions

| | Average Apparent Permeability Coefficient $P_{app}$ ($10^{-6}$ cm/s) | | |
|---|---|---|---|
| | pH 5.0 | pH 7.4 | pH 9.0 |
| Diphenhydramine | 3.26 ± 0.654 | 26.5 ± 4.51 | 29.7 ± 5.28 |
| Propranolol | 1.45 ± 0.765 | 9.35 ± 1.03 | 21.5 ± 4.66 |
| Atenolol | 2.10 ± 0.863 | 1.83 ± 1.15 | 3.02 ± 1.48 |
| Caffeine | 27.3 ± 4.10 | 23.7 ± 2.20 | 33.3 ± 3.55 |

The Permeability Test showed that donor pH had an effect on the apparent permeability coefficient ($P_{app}$) of diphenhydramine across buccal tissue. The $P_{app}$ of diphenhydramine was $3.26 \times 10^{-6}$ cm/s at pH 5.0, and increased to $26.5 \times 10^{-6}$ cm/s and $29.7 \times 10^{-6}$ cm/s at pH 7.4 and 9.0, respectively. The $P_{app}$ of propranolol, the positive control, was $1.45 \times 10^{-6}$ cm/s at pH 5.0, and increased to $9.35 \times 10^{-6}$ cm/s and $21.5 \times 10^{-6}$ cm/s at pH 7.4 and 9.0, respectively. In contrast, the $P_{app}$ of the reference compounds, atenolol and caffeine, only moderately increased at pH 9.0 compared to that at pH 5.0 and 7.4.

It was found that the permeability of diphenhydramine across buccal tissue increased more than 8 fold by adjusting the pH from 5.0 and 7.4. Such an increase in permeability was unexpected because less than 1% of diphenhydramine would be unionized under these conditions. Based on the pKa value of diphenhydramine, the highest fraction of unionized diphenhydramine would be present at pH 9.0. However, it was found that increasing the pH from 7.4 to 9.0 did not significantly increase the $P_{app}$.

Permeability Enhancer Test

Different permeability enhancers were tested to assess the effect on unidirectional permeability of diphenhydramine across buccal tissue. In order to test the effect of permeability enhancers on the unidirectional permeability of diphenhydramine across buccal tissue, the Permeability Enhancer Test was performed. Cell culture experiments were performed using buccal tissue plated on Millipore Millicell® plates. First, a dosing solution containing diphenhydramine, a permeability enhancer and reference compounds was added to the apical surface of the tissue. Then, the transport of diphenhydramine and reference compounds across the tissue was monitored over time by sampling the receiver solution. The test was performed according to the Permeability Enhancer Assay as described hereafter.

Table 2 summarizes the results from this test.

TABLE 2

Unidirectional Permeability of Diphenhydramine in the presence of Permeability Enhancers

| Permeability Enhancer (Concentration) | Average Apparent Permeability Coefficient (cm/s) |
|---|---|
| Cetylpyridinium chloride (0.5%) | $6.04 \times 10^{-6} \pm 3.30$ |
| Sodium Caprate (50 mM) | $4.30 \times 10^{-6} \pm 0.938$ |
| SDS (1%) | $0.382 \times 10^{-6} \pm 0.141$ |
| Myrj™ S8 (2.25%) | $1.40 \times 10^{-6} \pm 0.300$ |
| Menthol (2%) | $3.14 \times 10^{-6} \pm 0.336$ |
| Citrate Buffer (0.1M) | $0.227 \times 10^{-6} \pm 0.0543$ |
| Oleic Acid (5%) | $0.481 \times 10^{-6} \pm 0.227$ |

The Permeability Enhancer Test showed that at a pH of 5.0, the addition of certain permeability enhancers increased the $P_{app}$ of diphenhydramine across buccal tissue. When using a $P_{app}$ of $3.26 \times 10^{-6}$ cm/s as a reference obtained from the Permeability Test, the $P_{app}$ of diphenhydramine was higher when either cetylpyridinium chloride or sodium caprate was present. In contrast, the $P_{app}$ of diphenhydramine was lower in the presence of citrate, oleic acid, sodium dodecyl sulfate (SDS), or Myrj™ S8. Menthol had minimal effect on the $P_{app}$ of diphenhydramine Although menthol is not the most effective permeability enhancer, it could be used to provide flavor benefits or to act as a decongestant.

It was found that only some permeability enhancers increased the $P_{app}$ of diphenhydramine, even though all the permeability enhancers tested are known to increase buccal absorption. When cetylpyridinium chloride was included in the dosing solution, the $P_{app}$ increased to $6.04 \times 10^{-6}$ cm/s, 1.8 fold higher than without the permeability enhancer at the same pH. In addition, when sodium caprate was added to the dosing solution, $P_{app}$ increased to $4.30 \times 10^{-6}$ cm/s.

Disintegration and Dissolution

Oral dosage forms containing 25 mg diphenhydramine were tested to assess disintegration and dissolution.

First, tablets A, B and C were made according to the procedure described in the examples hereafter. To improve compression of the tablet, the ratio of mannitol and Pro-Solv® SMCC 90 was varied. It was found that Tablet A and B did not tablet well under desired compression force. In addition, Tablet A and B failed to provide tablets with acceptable quality (i.e. hardness and friability) that would allow for further processing. It was found that the formula of Tablet C, with ratio of mannitol to ProSolv® SMCC 90 of 1:1, created the best compressed tablet.

Second, the tablet breaking force and disintegration of Tablet C was tested according to the Disintegration Method and Tablet Breaking Force Test Method described hereafter.

Table 3 summarizes the results from this test.

TABLE 3

Disintegration Time of Tablet C

| | Tablet Breaking Force (kp) | Disintegration (Seconds) |
|---|---|---|
| Replicate 1 | 0.8 | 9 |
| Replicate 2 | 1.3 | 12 |
| Replicate 3 | 2.1 | 11 |
| Replicate 4 | 2.4 | 12 |
| Average | 1.65 | 11 |

It was found that Tablet C had an average tablet breaking force of 1.65 kp and an average disintegration time of 11 seconds.

Third, the dissolution of diphenhydramine in Tablet C was tested according to the Dissolution Method described hereafter. Compressed tablets with a hardness of 0.8 kp to 2.4 kp were tested. The Dissolution Test showed that diphenhydramine was completely dissolved within 30 seconds. Complete dissolution is measured according to the United States Pharmacopeia ("USP") <711> Dissolution (official from Dec. 1, 2011) stage 1 acceptance criteria and requires at least Q+5% of the active ingredient to be considered "completely dissolved", where Q is the amount dissolved of the active ingredient. Diphenhydramine has a Q of 75%. Thus, complete dissolution is defined as 80% for diphenhydramine.

Taste Testing

Flavoring systems were tested to assess the ability to mitigate the bitterness and numbing effect of diphenhydramine in the oral cavity. In order to test the effect of flavoring systems, taste tests were performed on 7 participants. The participants placed 1 ml of each sample under their tongue and held the liquid for 1 minute without swallowing. The participants then expectorated the liquid into a cup and completed a questionnaire. The participants were asked to rate on a scale of 0 (none) to 10 (a lot) the amount of bitterness and numbing for each sample and control. The positive control had the highest amount of diphenhydramine, and therefore, would have the most bitter and numbing effect. The negative control had the least amount of diphenhydramine, and therefore, would have the least bitter and numbing effect. The samples tested were prepared according to the formulas as described in Samples 1-5 hereafter.

Table 4 summarizes the results from this test.

TABLE 4

Taste Test Results

| | Avg. Bitterness Δ vs. Positive Control | Avg. Numbing Δ vs. Positive Control |
|---|---|---|
| Sample 2 (Negative Control) | −6 | −8 |
| Sample 3 | −2 | −4 |
| Sample 4 | −3 | −5 |
| Sample 5 | −5 | −8 |

The addition of citrate in Sample 4 was found to mitigate bitterness and numbing slightly better than without citrate in Sample 3. Although citrate is not an effective permeability enhancer, it could be used to mitigate the bitterness and numbing effect of diphenhydramine.

It was found that that Sample 5 had the greatest average difference relative to the positive control. High fructose corn syrup was found to mitigate bitterness and numbing in Samples 3 and 4, but not to the same extent as the full flavoring system in Sample 5. It is believed that flavor and sweetener further diminish the unpleasant bitterness and numbing of diphenhydramine.

Permeability Assay

EpiOral® tissues (Epi-Oral ORL-200; Lot #21116 Kit D) were purchased from MatTek Corporation (Ashland, Mass.). The tissues were received in 24-well plates on collagen coated, 9 mm ID single well tissue culture plate inserts (Pore size=0.4 µm, Inner Diameter=0.875 cm; Surface area=0.6 cm; EMD Millipore Millicell®) in MatTek culture media. Tissues were cultured according to instructions from MatTek. The Permeability Assay was performed on the second day after arrival of the cultures.

Prior to the Permeability Assay, the tissues were equilibrated in pre-warmed EpiOral® assay medium (provided by MatTek) for one hour at 37° C. Following equilibration, the EpiOral® tissues were transferred to a 24-well plate with 750 µl of Incubation Buffer in each well, the medium was aspirated, and 350 µl of dosing solution (See Table 6) was added to each insert. Incubation buffers consisted of Dulbecco's phosphate-buffered saline (MatTek; Lot #110414 maa) without $CaCl_2$ and $MgCl_2$ adjusted to pH 5.0, 7.4, and 9.0 for the donor, and pH 7.4 for the receiver. Receiver samples (200 µl) were collected at 30, 60, and 120 minutes, and replaced with an equal volume of fresh pre-warmed receiver buffer (at 30 and 60 minutes). The donor side was sampled (50 µl) at 0 and 120 minutes. The assay was conducted at 37° C. in a humidified $CO_2$ incubator.

Unidirectional permeation assessment for diphenhydramine across EpiOral® tissue was conducted according to Table 5, with atenolol (low-permeability reference compound), caffeine (high-permeability reference compound), and propranolol (positive control) co-dosed with diphenhydramine Samples were assayed by liquid chromatography—mass spectrometry (LC-MS/MS) using a Sciex API4000 LC-MS/MS. Liquid chromatography was performed using a Waters Acquity HSS T3 column, 1.8 µm, 50×2.1 mm (available from Waters, Milford, Mass.). The mobile phases were A, 0.1% formic acid in water and B, 0.1% formic acid in acetonitrile. The following conditions are used:

| Gradient Conditions | Time (mm) | % A | % B |
|---|---|---|---|
| | 0.0 | 90 | 10 |
| | 0.40 | 90 | 10 |
| | 0.80 | 0 | 100 |
| | 1.00 | 0 | 100 |
| | 1.20 | 90 | 10 |
| | 1.50 | 90 | 10 |
| Run Time (minutes) | | 1.50 | |
| Column Temperature (° C.) | | 40 | |
| Sample compartment temperature (° C.) | | 5 | |
| Flow Rate (µL/min) | | 800 | |
| Detector Wavelength (nm) | | 225 | |
| Injection volume (µL) | | 5 | |

Samples were then analyzed by mass spectrometry. The interface was set to "Electrospray" and the mode was set to "Multiple Reaction Monitoring." The gases were: CUR 30, GS1 50, GS2 50, CAD 10. The source temperature is 550° C. The voltages and ions monitored were as follows:

TABLE 5

Treatments

| Dosing Solution | n | Donor pH | Receiver pH | Donor Time Points (Min) | Receiver Time Points (Min) |
|---|---|---|---|---|---|
| Diphenhydramine hydrochloride[1] (100 µM), propranolol[2] (100 µM), atenolol[3] (100 µM), and caffeine[4] (50 µM) | 6 | 5.0 | 7.4 | 0 and 120 | 30, 60, and 120 |
| Diphenhydramine hydrochloride[1] (100 µM), propranolol[2] (100 µM), atenolol[3] (100 µM), and caffeine[4] (50 µM) | 6 | 7.4 | 7.4 | 0 and 120 | 30, 60, and 120 |
| Diphenhydramine hydrochloride[1] (100 µM), propranolol[2] (100 µM), atenolol[3] (100 µM), and caffeine[4] (50 µM) | 6 | 9.0 | 7.4 | 0 and 120 | 30, 60, and 120 |
| Atenolol[3] (100 µM), and caffeine[4] (50 µM) (Negative Control) | 6 | 7.4 | 7.4 | 0 and 120 | 30, 60, and 120 |

[1]Lot # M121006; M.W. 291.82
[2]Sigma Lot # BCBJ2807V; M.W. 295.80
[3]Sigma-Aldrich (St. Louis, MO)
[4]Sigma-Aldrich (St. Louis, MO)

| Analyte | Polarity | Precursor Ion | Product Ion | IS[1] (V) | DP[2] (V) | EP[3] (V) | CE[4] (V) | CXP[5] (V) |
|---|---|---|---|---|---|---|---|---|
| Diphenhydramine | Positive | 256.2 | 152.2 | 5500 | 35 | 10 | 75 | 10.2 |
| Propranolol | Positive | 260.2 | 116.1 | 5500 | 35 | 10 | 32 | 3 |
| Atenolol | Positive | 267.2 | 145.1 | 5500 | 60 | 10 | 46 | 9.7 |
| Caffeine | Positive | 195.1 | 138.1 | 5500 | 75 | 10 | 27 | 9 |
| Warfarin | Positive | 309.2 | 251.1 | 5500 | 50 | 10 | 29 | 3 |

[1] Ion Spray Voltage
[2] Declustering Potential
[3] Entrance Potential
[4] Collision Energy
[5] Collision Cell Exit Potential The apparent permeability coefficient ($P_{app}$) was calculated as follows:

$$P_{app} = (dC_r/dt) \times V_r/(A \times C_{ini})$$

Where, $dC_r/dt$ is the slope of cumulative concentration in the receiver compartment over time in $\mu Ms^{-1}$; $V_r$ is the volume of the receiver compartment; A is the diffusional area of the membrane; and $C_{ini}$ is the donor concentration at 0 minute in $\mu M$.

Permeability Enhancer Assay

EpiOral® tissues (Epi-Oral ORL-200; Lot #21145 Kit D) were purchased from MatTek Corporation (Ashland, Mass.). The tissues were received in 24-well plates on collagen coated, 9 mm ID single well tissue culture plate inserts (Pore size=0.4 μm, Inner Diameter=0.875 cm; Surface area=0.6 cm; EMD Millipore Millicell®) in MatTek culture media. Tissues were cultured according to instructions from MatTek. The Permeability Enhancer Assay was performed on the second day after arrival of the cultures.

Prior to the Permeability Enhancer Assay, the tissues were equilibrated in pre-warmed EpiOral® assay medium (provided by MatTek) for one hour at 37° C. Following equilibration, the EpiOral® tissues were transferred to a 24-well plate with 750 μl of Incubation Buffer in each well, the medium was aspirated, and 300 μl of dosing solution was added to each insert. The dosing solution contained 100 μM Diphenhydramine hydrochloride (Lot #M121006; M.W. 291.82), 100 μM Atenolol (available from Sigma-Aldrich), 50 μM caffeine (available from Sigma-Aldrich), and a permeability enhancer. Incubation buffers consisted of Dulbecco's phosphate-buffered saline (MatTek; Lot #021015MAA) without $CaCl_2$ and $MgCl_2$ adjusted to pH 5.0 for the donor and pH 7.4 for the receiver. Permeability enhancers tested include: 1% Sodium dodecyl sulfate; 0.5% Cetylpyridinium chloride; 2.25% Myrj™ S8; 2% Menthol; 0.1M Citrate Buffer; 5% Oleic Acid; and 50 mM Na Caprate. Receiver samples (200 μl) were collected at 30, 60, and 120 minutes, and replaced with an equal volume of fresh pre-warmed receiver buffer (at 30 and 60 minutes). The donor side was not sampled and donor concentration was not measured. The assay was conducted at 37° C. in a humidified $CO_2$ incubator.

Unidirectional permeation assessment for diphenhydramine across EpiOral® tissue was conducted with atenolol (low-permeability reference compound) and caffeine (high-permeability reference compound) co-dosed with diphenhydramine and without diphenhydramine (negative control).

Samples were assayed by liquid chromatography—mass spectrometry (LC-MS/MS) using a Sciex API4000 LC-MS/MS. Liquid chromatography was performed following the same method and conditions as stated above in the Permeability Assay.

Samples were then analyzed by mass spectrometry. The interface was set to "Electrospray" and the mode was set to "Multiple Reaction Monitoring." The gases were: CUR 30, GS1 50, GS2 50, CAD 10. The source temperature is 550° C. The voltages and ions monitored were as follows:

| Analyte | Polarity | Precursor Ion | Product Ion | IS[1] (V) | DP[2] (V) | EP[3] (V) | CE[4] (V) | CXP[5] (V) |
|---|---|---|---|---|---|---|---|---|
| Diphenhydramine | Positive | 256.2 | 152.2 | 5500 | 35 | 10 | 75 | 10.2 |
| Atenolol | Positive | 267.2 | 145.1 | 5500 | 60 | 10 | 46 | 9.7 |
| Caffeine | Positive | 195.1 | 138.1 | 5500 | 75 | 10 | 27 | 9 |
| Warfarin | Positive | 309.2 | 251.1 | 5500 | 50 | 10 | 29 | 3 |

[1] Ion Spray Voltage
[2] Declustering Potential
[3] Entrance Potential
[4] Collision Energy
[5] Collision Cell Exit Potential The apparent permeability coefficient ($P_{app}$) was calculated as follows:

$$P_{app} = (dC_r/dt) \times V_r/(A \times C_n)$$

Where, $dC_r/dt$ is the slope of cumulative concentration in the receiver compartment over time in $\mu Ms^{-1}$; $V_r$ is the volume of the receiver compartment; A is the diffusional area of the membrane; and $C_n$ is the nominal dosing concentration in $\mu M$.

Disintegration Method

Tablet disintegration time was determined according to the method described in USP <701> (Aug. 1, 2008). The disintegration procedure for uncoated tablets was performed by placing 6 tablets (each tablet in a separate tube) in an Erweka ZT72 disintegrator (Milford, Conn.). The tablets were repeatedly immersed in 37° C. deionized water at a rate of 30 strokes per minute until the tablets disintegrated. Disintegration end point was determined visually.

Dissolution Method

The dissolution profiles for diphenhydramine can be determined according to the following method, which uses the method described in USP 35 Monograph Chapter <711> Dissolution, Apparatus 2 (Paddle Apparatus) (official from Dec. 1, 2011).

Assemble the apparatus then place 900 mL of pre-warmed (37.0±0.5° C.) distilled water into the vessel. Set the paddle speed to 75 revolutions per minute (RPM). Commence dissolution testing by dropping one oral dosage form into the vessel. Stainless steel, spring style capsule sinkers that are 23 mm long by 8 mm wide (commercially available as Sotax style sinker, part # CAPWST-23 from QLA, Telford, Pa.) can be used to prevent the capsules from floating in the vessels. At each time point, withdraw a 10 mL aliquot of sample from the vessel using a 10 mL syringe connected to a stainless steel cannula with attached 10 μm filters (available from QLA). Time points can be 15, 30, 60 seconds, 5 and 15 minutes.

The HPLC Dissolution Assay, as described herein, can be used to determine the percent dissolved values of diphenhydramine in each sample.

HPLC Dissolution Assay

This method is applicable for the determination of diphenhydramine in sample aliquots from the Dissolution Method. The samples can be analyzed by high-performance liquid chromatography (HPLC). The HPLC column can be a Waters XBridge Phenyl, 3.5 μm 4.6 mm×150 mm (available from Waters, Milford, Mass.).

First, the stock and working standard solutions are prepared. These solutions should be prepared fresh at time of use.

Standard Solution Preparation

Stock Solution (0.278 mg/mL)

Weigh 27.8 mg±0.5 mg of the Diphenhydramine Reference Standard into a 100 mL volumetric flask. Fill to volume with distilled water and gently swirl, or sonicate if necessary, to dissolve.

Working Standard Solution (0.028 mg/mL)

Transfer 5 mL of the Stock Standard into a 50 mL volumetric flask. Fill to volume with distilled water. Mix well.

Set up the HPLC system as per the conditions in the table below.

| Gradient Conditions | Time (mm) | % A (0.1% TFA) | % B (Acetonitrile) |
|---|---|---|---|
| | 0.0 | 85 | 15 |
| | 1.0 | 85 | 15 |
| | 11.0 | 60 | 40 |
| | 15.0 | 10 | 90 |
| | 15.1 | 85 | 15 |
| | 17.0 | 85 | 15 |
| Run Time (minutes) | | 17 | |
| Column Temperature (° C.) | | 40 | |
| Sample compartment temperature | | Ambient | |
| Flow Rate (mL/min) | | 1.0 | |
| Detector Wavelength (nm) | | 225 | |
| Injection volume (μL) | | 20 | | pH Test Method

First, calibrate the Thermo Scientific Orion 320 pH meter. Do this by turning on the pH meter and waiting for 30 seconds. Then take the electrode out of the storage solution, rinse the electrode with distilled water, and carefully wipe the electrode with a scientific cleaning wipe, such as a Kimwipe®. Submerse the electrode in the pH 7 buffer and press the calibrate button. Wait until the pH icon stops flashing and press the calibrate button a second time. Rinse the electrode with distilled water and carefully wipe the electrode with a scientific cleaning wipe. Then submerse the electrode into the pH 4 buffer and wait until the pH icon stops flashing and press the measure button. Rinse the electrode with distilled water and carefully wipe with a scientific cleaning wipe. Now the pH meter is calibrated and can be used to test the pH of a solution.

Place a 25 mg diphenhydramine tablet into 10 mL of distilled water. The tablet is not crushed and the water is 23° C. The solution is not stirred at any time. The pH is measured at 5 minutes.

Tablet Breaking Force Test Method

Tablet breaking force was determined according to the method described in USP <1217> (Aug. 1, 2015) using a Vankel Benchsaver VK200 Tablet Hardness Tester.

Examples

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, i.e., wt/wt percentages, unless otherwise specified.

The following compositions can be prepared in accordance with the present invention:

| Ingredient | Tablet A % w/w | Tablet B % w/w | Tablet C % w/w | Tablet D % w/w | Tablet E % w/w |
|---|---|---|---|---|---|
| Mannitol | 59.5 | 49.5 | 39.5 | 39.5 | 39.5 |
| Sucrose | 4.0 | 4.0 | 4.0 | 4.0 | 4.0 |
| Crospovidone | 4.0 | 4.0 | 4.0 | 4.0 | 4.0 |
| ProSolv ® SMCC 90 | 19.0 | 29.0 | 39.0 | 38.0 | 38.0 |
| Diphenhydramine | 12.5 | 12.5 | 12.5 | 12.5 | 12.5 |
| Sodium Caprate | 0 | 0 | 0 | 1.0 | 0 |
| Cetylpyridinium Chloride | 0 | 0 | 0 | 0 | 1.0 |
| Magnesium Stearate | 1.0 | 1.0 | 1.0 | 1.0 | 1.0 |
| Total | 100 | 100 | 100 | 100 | 100 |

| Ingredient | Sample 1 (Positive Control) w/w % | Sample 2 (Negative Control) w/w % | Sample 3 w/w % | Sample 4 w/w % | Sample 5 w/w % |
|---|---|---|---|---|---|
| Propylene Glycol | 0 | 5.0% | 0 | 0 | 5.0% |
| Ethanol | 0 | 7.545% | 0 | 0 | 7.545% |
| Diphenhydramine HCL | 2.50% | 0.1473% | 2.204% | 2.204% | 2.2085% |
| Flavor | 0 | 0.20% | 0 | 0 | 0.20% |
| Water Purified | 97.5% | 45.1048% | 56.5531% | 56.0131% | 43.0436% |
| Sodium Citrate Dihydrate | 0 | 0.19% | 0 | 0.19% | 0.19% |
| Citric Acid | 0 | 0.35% | 0 | 0.35% | 0.35% |
| Polyoxyl 40 Stearate | 0 | 0.05% | 0 | 0 | 0.05% |
| Sodium Saccharin | 0 | 0.07% | 0 | 0 | 0.07% |

-continued

| Ingredient | Sample 1 (Positive Control) w/w % | Sample 2 (Negative Control) w/w % | Sample 3 w/w % | Sample 4 w/w % | Sample 5 w/w % |
|---|---|---|---|---|---|
| Sodium Benzoate | 0 | 0.10% | 0 | 0 | 0.10% |
| High Fructose Corn Syrup | 0 | 41.2429% | 41.2429% | 41.2429% | 41.2429% |

Tablets A, B and C were made according to the following procedure. The tablets were prepared by weighing all formulation ingredients together, except the magnesium stearate, on a weighing pan. Typically, a tablet formulation batch was 1000 g total weight so that multiple tablets could be prepared for testing. The ingredients were placed into a 4 quart V-blender for 5 minutes. Then, the magnesium stearate was added and blended in the V-blender for an additional one minute. Tablets were formed from the resulting formulation on a Riva Piccola B/D tablet press fitted with 10 mm standard round concave die punches compacting over a range of compression forces. Tablet weight was set at 200 mg by adjusting the tablet press.

Tablets D and E could be made by following the method of Tablets A-C. Permeability enhancers can be added to the other formulation ingredients prior to adding the magnesium stearate. The formulations can be adjusted by adding the buffering agent to achieve a pH as the tablet dissolves in the range of about 7.0 to about 8.0.

Liquid samples 1-5 were prepared according to the following procedure.

For samples 2 and 5, propylene glycol and ethanol were added to a two-liter stainless steel vessel and mixed at 200 RPM. The drug active, Diphenhydramine HCl, was added to the batch and mixed until dissolved. The flavor, water, sodium citrate dihydrate, and citric acid were then added and mixed until dissolved. Following this mixing, the surfactant, polyoxyl 40 stearate was added to the batch and mixed until dissolved. The sweetener, sodium saccharin, and preservative, sodium benzoate, were added to the batch and mixed until dissolved. Following dissolution of all solids, high fructose corn syrup was added to the batch and mixed at 200 RPM until homogeneous. Total mix time for these batches was approximately 10 minutes.

For samples 1, 3 and 4, water was added to a two-liter stainless steel vessel and mixed at 200 RPM. The drug active, Diphenhydramine HCl, was then added and mixed until dissolved. Following this mixing, the additional solids (if present in the formulation) were added and mixed until dissolved. Following dissolution of all solids, the final excipient, high fructose corn syrup (if present in the formulation), was added to the batch and mixed at 200 RPM until homogenous.

Total mix time for these batches was approximately 10 minutes.

Combinations

A. An oral dosage form comprising: a therapeutically effective amount of diphenhydramine or a pharmaceutically acceptable salt thereof; a buffering agent sufficient to achieve a pH of from 7.0 to 8.0 as determined by the pH Test Method; wherein the diphenhydramine is completely dissolved within 2 minutes as determined by the Dissolution Method.

B. The oral dosage form according to paragraph A, wherein the diphenhydramine is completely dissolved within 1 minute; preferably within 45 seconds; and more preferably within 30 seconds.

C. The oral dosage form according to paragraph A or B, further comprising a permeability enhancer.

D. The oral dosage form according to paragraph C, wherein the permeability enhancer is selected from the group consisting of sodium caprate, cetylpyridinium chloride and combinations thereof.

E. The oral dosage form according to paragraph C or D, wherein the ratio of diphenhydramine to permeability enhancer is from 1:5 to 1:30, preferably 1:10 to 1:25, and more preferably 1:12.5 to 1:20.

F. The oral dosage form of any one of preceding paragraphs A-E, wherein the buffering agent is selected from the group consisting of meglumine, glycine, sodium carbonate, calcium carbonate, sodium bicarbonate, phosphate buffer, magnesium hydroxide, and combinations thereof.

G. The oral dosage form of any one of the preceding paragraphs A-F, wherein the apparent permeability coefficient of diphenhydramine across buccal tissue is $3 \times 10^{-6}$ cm/s to $40 \times 10^{-6}$ cm/s; preferably $22 \times 10^{-6}$ cm/s to $35 \times 10^{-6}$ cm/s; and more preferably $25 \times 10^{-6}$ cm/s to $30 \times 10^{-6}$ cm/s as determined by the in vitro Permeability Assay.

H. The oral dosage form of any one of the preceding paragraphs A-G, wherein the oral dosage form comprises from 5.0 mg to 50 mg diphenhydramine; preferably from 10 mg to 30 mg diphenhydramine; and more preferably from 12.5 mg to 25 mg diphenhydramine.

I. The oral dosage form of any one of the preceding paragraphs A-H, wherein the oral dosage form is administered to a subject sublingually.

J. The oral dosage form of any one of the preceding paragraphs A-I, wherein the oral dosage form is selected from the group consisting of tablets, pills, capsules, lyophilized tablets, lozenges, candies, powders, granular substances, films, dispersible fluids, sprays, quick dissolving fibers and combinations thereof.

K. The oral dosage form of paragraph J, wherein the oral dosage form is a lyophilized tablet.

L. The oral dosage form of any one of the preceding paragraphs A-K, wherein the oral dosage form comprises particles with a diameter from 45 μm to 105 μm.

M. The oral dosage form of any one of the preceding paragraphs A-L, wherein the oral dosage form disintegrates in less than 30 seconds.

N. A method for inducing sleep of a subject in need thereof comprising placing the oral dosage form of paragraph A in the subject's oral cavity.

O. A package for a pharmaceutical composition comprising a packaging material and the oral dosage form of paragraph A contained within the packaging material; wherein the packaging material comprises usage indicia which indicate the steps of (i) placing the oral dosage form under a subject's tongue, (ii) holding the oral dosage form under the tongue for less than about 1 minute, (iii) optionally avoiding eating, drinking, and/or talking in order to keep the oral dosage form in place, (iv) swallowing the oral dosage form, (v) optionally administering the oral dosage form at night; (vi) optionally administering the oral dosage form in response to an allergic reaction, and/or (vii) optionally taking the oral dosage form every 4 to 6 hours as needed.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for inducing sleep of a subject in need thereof comprising: placing an oral dosage form in a subject's oral cavity, wherein the oral dosage form comprises a therapeutically effective amount of diphenhydramine or a pharmaceutically acceptable salt thereof; a permeability enhancer selected from the group consisting of sodium caprate, cetylpyridinium chloride, and combinations thereof; and a buffering agent sufficient to achieve a pH of about 7.0 to about 8.0.

2. The method of claim 1, wherein the oral dosage form is placed under the tongue.

3. The method of claim 2, wherein the oral dosage form is held under the tongue for less than about 1 minute.

4. The method of claim 1, wherein the oral dosage form is lyophilized.

5. The method of claim 1, wherein the oral dosage form comprises a ratio of diphenhydramine to permeability enhancer of from about 1:10 to about 1:25.

6. The method of claim 1, wherein the therapeutically effective amount of diphenhydramine or a pharmaceutically acceptable salt thereof is from about 12.5 mg to about 50 mg.

7. The method of claim 6, wherein the therapeutically effective amount of diphenhydramine or a pharmaceutically acceptable salt thereof is from about 25 mg to about 50 mg.

8. The method of claim 7, wherein the oral dosage form comprises from about 0.1% to about 10% of the permeability enhancer, by weight of the oral dosage form.

9. The method of claim 8, wherein the oral dosage form comprises from about 0.75% to about 3% of the permeability enhancer, by weight of the oral dosage form.

10. The method of claim 9, wherein the oral dosage form comprises one or more additional actives.

11. The method of claim 6, wherein the oral dosage form comprises from about 1% to about 20% disintegrant, by weight of the oral dosage form.

* * * * *